US012773334B2

(12) United States Patent
Collins et al.

(10) Patent No.: US 12,773,334 B2
(45) Date of Patent: Oct. 27, 2026

(54) ANTI-MIGRATION STENT

(71) Applicant: Boston Scientific Scimed, Inc., Maple Grove, MN (US)

(72) Inventors: David Collins, Galway (IE); Darren G. Curran, Galway (IE); Fionn Stapleton, Galway (IE); Ryan Desmond Lynch, Roscommon (IE); John O'Driscoll, Galway (IE); Aran Murphy, Wexford (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 564 days.

(21) Appl. No.: 18/352,190

(22) Filed: Jul. 13, 2023

(65) Prior Publication Data

US 2024/0016637 A1 Jan. 18, 2024

Related U.S. Application Data

(60) Provisional application No. 63/389,285, filed on Jul. 14, 2022.

(51) Int. Cl.
*A61F 5/00* (2006.01)

(52) U.S. Cl.
CPC .................................. *A61F 5/0076* (2013.01)

(58) Field of Classification Search
CPC ....... A61M 27/002; A61F 5/0076; A61F 2/82; A61F 2/04; A61F 2/93; A61B 17/11
See application file for complete search history.

(56) References Cited

U.S. PATENT DOCUMENTS

| | | | | |
|---|---|---|---|---|
| 2012/0296257 | A1 | 11/2012 | Van Dam et al. | |
| 2020/0170776 | A1* | 6/2020 | Folan | A61F 2/93 |
| 2022/0079784 | A1 | 3/2022 | Folan | |
| 2022/0087852 | A1* | 3/2022 | Gilmartin | A61F 5/445 |

FOREIGN PATENT DOCUMENTS

| | | |
|---|---|---|
| JP | 2022501113 A | 1/2022 |

OTHER PUBLICATIONS

International Search Report and Written Opinion dated Oct. 9, 2023 for International Application No. PCT/US2023/070169.

* cited by examiner

*Primary Examiner* — Leslie R Deak
(74) *Attorney, Agent, or Firm* — Seager, Tufte & Wickhem, LLP

(57) ABSTRACT

An example medical device may include a stent including a radially expanding tubular framework having a radially outward surface, a radially inward surface, a first end region, a second end region, a medial region positioned between the first end region and the second end region, and a lumen extending from the first end region to the second end region. A first flange structure may be positioned near the first end region, and a second flange structure may be positioned near the second end region. One of the first end region or the second end region may include a third flange structure.

18 Claims, 6 Drawing Sheets

ANTI-MIGRATION STENT

CROSS REFERENCE TO RELATED APPLICATIONS

This application claims the benefit of U.S. Provisional Patent Application Ser. No. 63/389,285 filed on Jul. 14, 2022, the disclosure of which is incorporated herein by reference.

TECHNICAL FIELD

The present disclosure relates generally to the field of implantable medical devices, and related systems and methods, for adjusting accessibility through a passage of a medical device. More particularly, the present disclosure relates to devices, systems, and methods for controlling and/or changing a passage using a flow-regulating device such as a lumen-apposing device.

BACKGROUND

Treatment methods for various medical conditions, such as obesity, diabetes, or duodenal ulcers, involve bypassing the duodenum or restricting flow of materials through the duodenum. If the treatment requires complete bypass of the duodenum, then occlusion (e.g., full occlusion) of the pylorus may be indicated, and an anastomosis may be created, such as between the stomach and the jejunum. A lumen-apposing device may be placed between the stomach and the jejunum to allow for passage of materials (fluid, liquid, chyme, etc.) from the stomach and into the jejunum. One challenge presented by such devices is to prevent migration of the device distally into the small intestine or proximally into the stomach. Thus, there is an ongoing need to provide alternative medical devices as well as alternative methods for manufacturing and using medical devices.

BRIEF SUMMARY

This disclosure provides design, material, manufacturing method, and use alternatives for medical devices. An example medical device may include a stent including a radially expanding tubular framework having a radially outward surface, a radially inward surface, a first end region, a second end region, a medial region positioned between the first end region and the second end region, and a lumen extending from the first end region to the second end region. A first flange structure may be positioned near the first end region, and a second flange structure may be positioned near the second end region. One of the first end region or the second end region may include a third flange structure.

Alternatively or additionally to any of the embodiments above, the stent may be a self-expanding stent.

Alternatively or additionally to any of the embodiments above, the first flange and the second flange may be configured to atraumatically engage a bodily tissue.

Alternatively or additionally to any of the embodiments above, the third flange structure may be positioned near the first end region.

Alternatively or additionally to any of the embodiments above, the second end region may include a fourth flange structure.

Alternatively or additionally to any of the embodiments above, the third flange structure may be longitudinally spaced from the first flange structure within a range of 5 mm to 75 mm.

Alternatively or additionally to any of the embodiments above, the third flange structure may be longitudinally spaced from the first flange structure by at least 20 mm.

Alternatively or additionally to any of the embodiments above, the first flange structure curves toward the third flange structure such that a first end and a second end of the first flange structure is configured to engage with the third flange structure.

Alternatively or additionally to any of the embodiments above, the first flange structure may include a first outer diameter, the second flange structure may include a second outer diameter, and the third flange structure may include a third outer diameter, wherein the first outer diameter, the second outer diameter, and the third outer diameter differ from one another.

Alternatively or additionally to any of the embodiments above, the first, second, and third flange structures each have an outer diameter greater than an outer diameter of the medial region.

Alternatively or additionally to any of the embodiments above, the third outer diameter may be greater than the first outer diameter and the second outer diameter.

Alternatively or additionally to any of the embodiments above, the radially expanding tubular framework may be formed from a woven filament braid.

Alternatively or additionally to any of the embodiments above, a braid angle of the third flange structure may differ from a braid angle of the first and second flange structures.

An example stent may include a radially expanding tubular framework formed from a woven filament braid having a first end region, a second end region, a medial region positioned between the first end region and the second end region, and a lumen extending from the first end region to the second end region. A first flange structure having a first outer diameter may be positioned near the first end region, a second flange structure having a second outer diameter may be positioned near the second end region, and a third flange structure having a third outer diameter may be positioned near the first end region. The third flange structure may be longitudinally spaced from the first flange structure, and the third outer diameter may be greater than the first outer diameter and the second outer diameter.

Alternatively or additionally to any of the embodiments above, the first outer diameter, the second outer diameter, and the third outer diameter may each be greater than an outer diameter of the medial region.

Alternatively or additionally to any of the embodiments above, a braid angle of the third flange structure may differ from a braid angle of the first and second flange structures.

Alternatively or additionally to any of the embodiments above, the third flange structure may be longitudinally spaced from the first flange structure within a range of 5 mm to 75 mm.

Alternatively or additionally to any of the embodiments above, the third flange structure may be longitudinally spaced from the first flange structure by at least 20 mm.

An example stent may include a radially expanding tubular framework formed from a woven filament braid having a first end region, a second end region, a medial region positioned between the first end region and the second end region, and a lumen extending from the first end region to the second end region. A first flange structure having a first outer diameter may be positioned near the first end region, a second flange structure having a second outer diameter may be positioned near the second end region, and a third flange structure having a third outer diameter may be positioned near the first end region. The third flange structure may be longitudinally spaced from the first flange structure within a range of 5 mm to 75 mm, and the first flange structure may curve toward the third flange structure such that a first end and a second end of the first flange structure may be configured to engage with the third flange structure.

Alternatively or additionally to any of the embodiments above, the third flange structure may be longitudinally spaced from the first flange structure by at least 20 mm.

Alternatively or additionally to any of the embodiments above, the third outer diameter may be greater than the first outer diameter and the second outer diameter.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
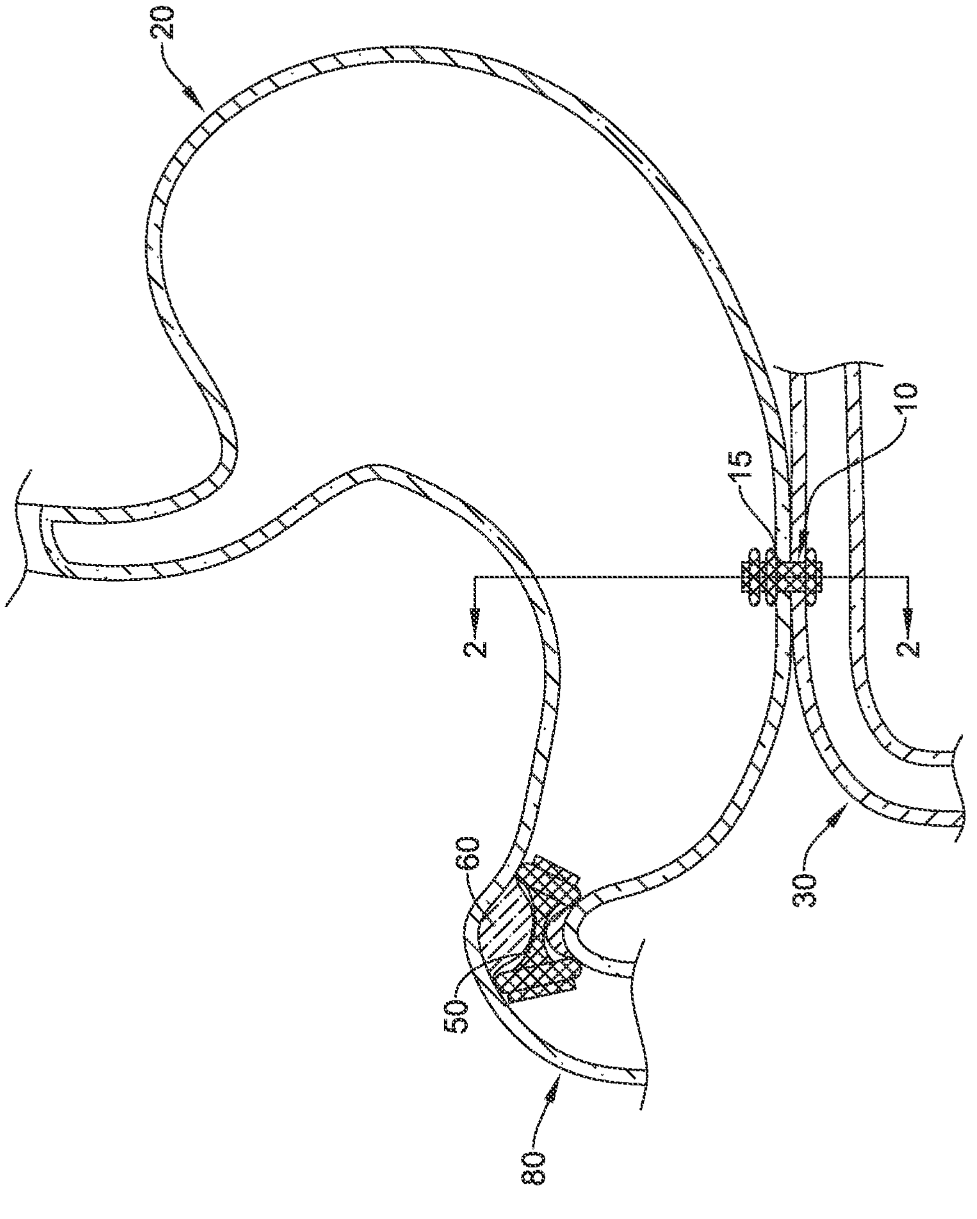
FIG. 1 illustrates a side view of a stent positioned between a stomach and a portion of a small intestine.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit of the disclosure.

DETAILED DESCRIPTION

For the following defined terms, these definitions shall be applied, unless a different definition is given in the claims or elsewhere in this specification.

All numeric values are herein assumed to be modified by the term “about,” whether or not explicitly indicated. The term “about” generally refers to a range of numbers that one of skill in the art would consider equivalent to the recited value (i.e., having the same function or result). In many instances, the term “about” may include numbers that are rounded to the nearest significant figure.

The recitation of numerical ranges by endpoints includes all numbers within that range (e.g., 1 to 5 includes, 1, 1.5, 2, 2.75, 3, 3.80, 4, and 5).

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise.

It is noted that references in this specification to “an embodiment”, “some embodiments”, “other embodiments”, etc., indicate that the embodiment described may include one or more features, structures, and/or characteristics. However, such recitations do not necessarily mean that all embodiments include the features, structures, and/or characteristics. Additionally, when features, structures, and/or characteristics are described in connection with one embodiment, it should be understood that such features, structures, and/or characteristics may also be used in connection with other embodiments whether or not explicitly described unless clearly stated to the contrary.

In accordance with various principles of the present disclosure, an implantable device may be used to extend across an anatomical structure to control or regulate the size of a passage therethrough. For instance, an implantable device may extend across a body passage or lumen, such terms being used interchangeably herein without intent to limit. The body passage or lumen may include, without limitation, a portion of a passage or lumen, a passage or lumen between anatomical structures (passages, lumens, cavities, organs, etc.), a passage created across apposed tissue walls (such as to create an anastomosis) etc. The device has a passage or lumen (such terms being used interchangeably herein without intent to limit) therethrough which may be used to occlude or block or narrow or close or constrict or regulate or control (such terms and conjugations thereof may be used interchangeably herein without intent to limit) the body passage through which the device is positioned. The device may be considered and referenced as an occlusion or lumen-apposing or anastomosis or flow-regulating or flow-controlling device, and such terms and various other alternatives thereto may be used interchangeably herein without intent to limit.

The following detailed description should be read with reference to the drawings in which similar elements in different drawings are numbered the same. The drawings, which are not necessarily to scale, depict illustrative embodiments and are not intended to limit the scope of the invention.

Figure 2:
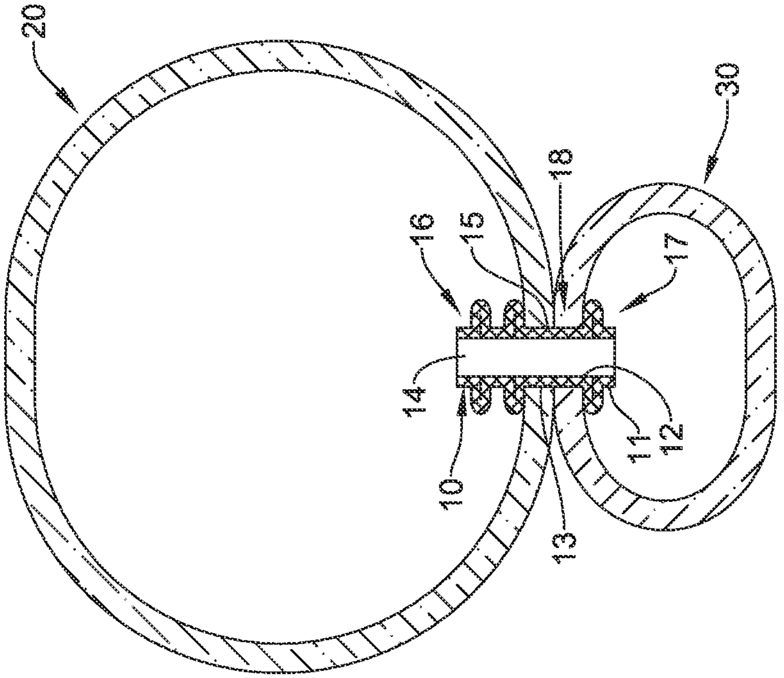
FIG. 2 illustrates a cross-section view of the stent positioned between the stomach and the portion of a small intestine take at line 2-2 of FIG. 1.

FIG. 1 illustrates a side view of an illustrative stent 10 positioned between a stomach 20 and a jejunum 30 (a portion of the small intestine), and FIG. 2 illustrates a cross-section view of the stent 10 positioned between the stomach 20 and the jejunum 30 taken at line 2-2 of FIG. 1. The stent 10 may be a self-expanding stent 10 and may include a radially expanding tubular framework 13 having a radially outward surface 11 and a radially inward surface 12. The radially expanding tubular framework 13 may include a first end region 16, a second end region 17, and a medial region 18 positioned between the first end region 16 and the second end region 17. The radially expanding tubular framework 13 may further include a lumen 14 extending from the first end region 16 to the second end region 17. The stomach 20 normally passes food materials (e.g., chyme, partially digested food materials, fluids, etc.) into a duodenum 40 through a pylorus 60. In some cases, treatment for a patient experiencing obesity, diabetes, or duodenal ulcers, may involve bypassing the duodenum 40, or restricting flow of materials through the duodenum 40. If the treatment requires complete bypass of the duodenum 40, then occlusion (e.g., full occlusion) of the pylorus 60 may be indicated, and an anastomosis 15 may be created between the stomach 20 and the jejunum 30, which may be known as a gastrojejunostomy. FIG. 1 illustrates an example bypass procedure in which a flow restricting device 50 has been positioned within the pylorus 60, thereby restricting access of food materials from the stomach 20 into the duodenum 40 (e.g., a complete bypass). A lumen-apposing metal stent (LAMS), such as the stent 10, may be placed between the stomach 20 and the jejunum 30, thereby forming the anastomosis 15, to allow for passage of food materials (fluid, liquid, chyme, etc.) from the stomach 20 and into the jejunum 30, as shown in FIGS. 1 and 2. While it is illustrated that the stent 10 may be used in forming the anastomosis 15 between the stomach 20 and the jejunum 30, it may be contemplated that the stent 10 may be used to treat a stenosis in a blood vessel, used to maintain a fluid opening or pathway in the vascular, urinary, biliary, tracheobronchial, esophageal or renal tracts, or position a device such as an artificial valve or filter within a body lumen, in some instances. Although illustrated as a stent, the stent 10 may be any of several devices that may be introduced endoscopically, subcutaneously, percutaneously or surgically to be positioned within an organ, tissue, or lumen, such as a heart, artery, vein, urethra, esophagus, trachea, bronchus, bile duct, or the like.

Figure 3:
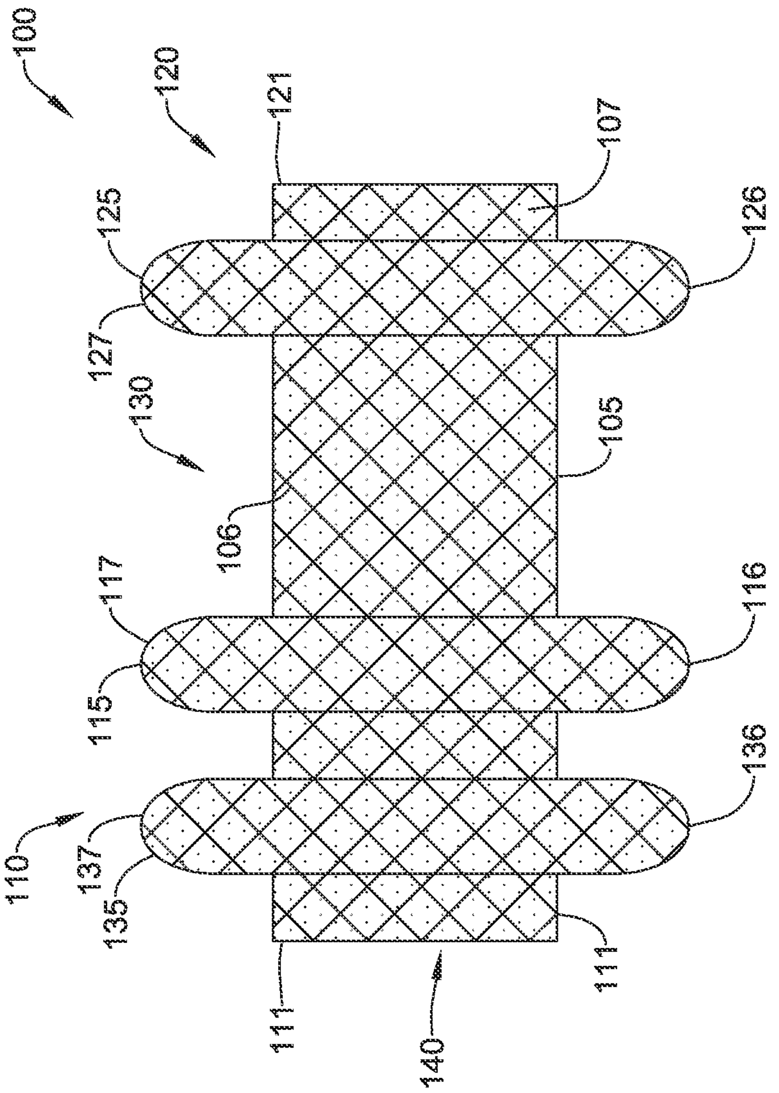
FIG. 3 illustrates a side view of an exemplary stent.

FIG. 3 illustrates a side view of an exemplary stent 100. The stent 100 may be an example of the stent 10 of FIGS. 1 and 2. The stent 100 may be a self-expanding stent 100 and may include a radially expanding tubular framework 105 having a radially outward surface 101 and a radially inward surface (not shown in FIG. 3). The radially inward surface may be considered as an example of the radially inward surface 12, as shown in FIG. 2. The term ‘radially expanding tubular framework 105’ may be referred to as ‘tubular framework 105’ hereafter. The stent 100 may include a height of 10 millimeters (mm) and an outer diameter (e.g., width) of 20 mm. In some cases, the height of the stent 100 may be 12 mm, 15 mm, 18 mm, or any other suitable height. In some cases, the outer diameter of the stent 100 may be 18 mm, 22 mm, 25 mm, or any other suitable diameter. The tubular framework 105 may include a first end region 110, a second end region 120, and a medial region 130 positioned between the first end region 110 and the second end region 120. The tubular framework 105 may further include a lumen 140 extending from the first end region 110 to the second end region 120. The lumen 140 may be considered as an example of the lumen 14, as shown in FIG. 2. In some cases, the first end region 110 may be a distal end region, and the second end region 120 may a proximal end region. In some cases, the first end region 110 may a proximal end region, and the second end region 120 may be a distal end region. The first end region 110 may include a first end 111 and the second end region 120 may include a second end 121. The first end region 110 may extend from the first end 111 to the medial region 130, and the second end region 120 may extend from the second end 121 to the medial region 130. In some cases, the medial region 130 may define a midpoint in the tubular framework 105, such that the first end region 110 and the second end region 120 may have the same lengths. In some cases, as indicated in FIG. 3, the medial region 130 may be disposed at a location other than a midpoint, such that the first and second end regions 110, 120 have different lengths.

In some cases, the first end region 110 may include a first flange structure 115 and the second end region 120 may include a second flange structure 125. The medial region 130 may be positioned between the first flange structure 115 and the second flange structure 125. The medial region 130 may be configured to engage with a tissue surface, thereby exerting a radial force to aid in prevention of migration of the stent 100. The first end region 110 may further include a third flange structure 135 that is longitudinally spaced from the first flange structure 115. The third flange structure 135 may provide additional radial force to the first end 110 of the stent 100 during peristalsis, thereby preventing migration of the stent 100 from the stomach to the jejunum during peristalsis or turbulence caused by the digestion of a food bolus. The third flange structure 135 may be longitudinally spaced from the first flange structure 115 within a range of 5 mm (millimeters) to 75 mm. In some cases, the third flange structure 135 may be longitudinally spaced from the first flange structure 115 by at least 20 mm. The longitudinal spacing between the first flange structure 115 and the third flange structure 135 may vary for the desired pullout force.

The first flange structure 115, the second flange structure 125, and the third flange structure 135 may be retention members configured to aid in holding the stent 100 in place. Thus, the first, second, and third flange structures 115, 125, 135 may include a width (e.g., an outer diameter) sufficient to provide retention strength. For example, the width of the first, second, and third flange structures 115, 125, 135 may be in the range of 20-70 mm (millimeters). In some cases, the first, second, and third flange structures 115, 125, 135 may include a width (e.g., outer diameter) greater than that of the first end 111, the second end 121, and the medial region 130 of the tubular framework 105. In some cases, the first, second, and third flange structures 115, 125, 135 may include the same width as one another, as indicated in FIG. 3. In some cases, the first and second flange structures 115, 125 may include the same width as one another, and the third flange structure 135 may include a width that differs from the width of the first and second flange structures 115, 125. In some cases, the first, second, and third flange structures 115, 125, 135 may all include differing widths.

In some cases, the first, second, and third flange structures 115, 125, 135 may include any of a variety of shapes, such as concave, convex, disc-shaped, cylindrical (e.g., having a longer longitudinal extent then illustrated), etc., or other configurations, the particular shape and configuration not being limited by the present disclosure. While it is illustrated that the first flange structure 115 and the third flange structure 135 are positioned near the first end region 110, and the second flange structure 125 is positioned near the second end region 120, it may be contemplated that the first flange structure 115 and the third flange structure 135 are positioned near the second end region 120, and the second flange structure 125 is positioned near the first end region 110. In some cases, it may be contemplated that the tubular framework 105 includes only one flange structure (e.g., the first flange structure 115, the second flange structure 125, or the third flange structure 135).

The stent 100 may be configured to be implanted between the stomach and the jejunum of a patient, to form an anastomosis. In some cases, the first flange structure 115 may abut a tissue surface (e.g., the stomach), the second flange structure 125 may abut a second tissue surface (e.g., the jejunum), and the medial region 130 of the stent 100 may extend through an opening within the stomach and the jejunum, and may be configured to engage with a tissue surface to form the anastomosis. In such cases, the third flange structure may be configured to extend into the stomach. In other embodiments, the stent 100 may be configured to be implanted in the urinary, biliary, tracheobronchial, esophageal or renal tracts, for example. Since the stent 100, or a portion thereof, may be intended to be implanted permanently in the body lumen, the stent 100 may be made, at least in part, from a biostable material. Examples of the biostable metal materials may include, but are not limited to, stainless steel, tantalum, tungsten, niobium, platinum, nickel-chromium alloys, cobalt-chromium alloys such as Elgiloy® and Phynox®, nitinol (e.g., 55% nickel, 45% titanium), and other alloys based on titanium, including nickel titanium alloys, or other suitable metals, or combinations or alloys thereof. Some suitable biostable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, or mixtures or combinations thereof.

The tubular framework 105 may include several interconnected struts 106 to form a woven filament braid structure of the tubular framework 105. The struts 106 may be configured to transition from a compressed state to an expanded state. The struts 106 may be formed of a metal material, such as nitinol or nitinol-containing material, or another nickel-titanium alloy, for example. The struts 106 may include a diameter of, for example, 0.0762 mm to 0.3556 mm. In some instances, the struts 106 may have a diameter of about 0.011 inches, for example. The number of struts 106 and the diameters of the struts 106, which may be the same or different, are not limiting, and other numbers of struts 106 and other wire diameters may suitably be used. Desirably, an even number of struts 106 may be used, for example, from about 10 to about 36 struts 106. In some cases, the tubular framework 105 may include a variety of braid angles forming the woven filament braid structure. For example, in some cases, the third flange structure 135 may include a braid angle that differs from a braid angle of the first flange structure 115 and the second flange structure 125. This may allow the third flange structure 135 to be stiffer, thereby acting as an anchor for the stent 100, whereas the first flange structure 115 may be softer, thereby providing more resistance to peristalsis. In some cases, the braid angle for the first, second, and third flange structures 115, 125, 135 may be the same. In some cases, the braid angle for the first, second, and third flange structures 115, 125, 135 may differ.

The tubular framework 105 may include a coating 107 applied over the struts 106 of the tubular framework 105, thus the entirety of the stent 100 may be covered with the coating 107. The coating 107 may be formed from a silicone and may be configured to prevent leakage of food materials during anastomosis formation. In some cases, the coating 107 may be applied over the struts 106 in the medial region 130. In some cases, the coating 107 may be applied over the struts 106 within the first end region 110 and the medial region 130, and in some cases, the coating 107 may be applied over the struts 106 within the second end region 120 and the medial region 130. These are just examples.

The first flange structure 115 may include a first end 116 and a second end 117, the second flange structure 125 may include a first end 126 and a second end 127, and the third flange structure 135 may include a first end 136 and a second end 137. The first ends 116, 126, 136 and the second ends 117, 127, 137 may be formed by bending the struts 106 of the tubular framework 105 to form atraumatic flange structures (e.g., first flange structure 115, second flange structure 125, third flange structure 135). Thus, the first ends 116, 126, 136 and the second ends 117, 127, 137 may be rounded and atraumatic, such that the first flange structure 115, the second flange structure 125, and the third flange structure 135 are configured to atraumatically engage a bodily tissue (e.g., stomach 20, jejunum 30).

Figure 4:
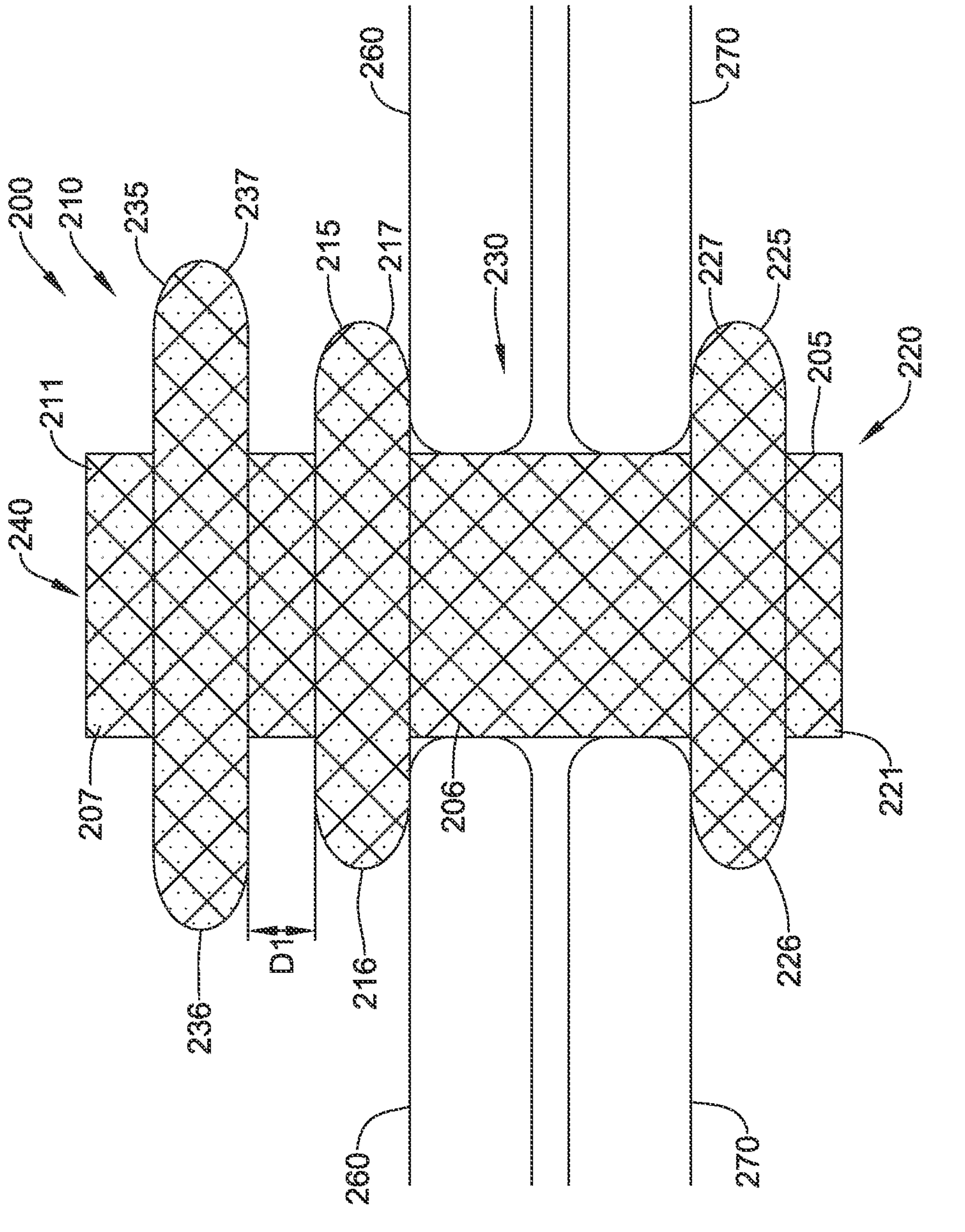
FIG. 4 illustrates an exemplary stent positioned between a gastric wall and a portion of a small intestine.

FIG. 4 illustrates an exemplary stent 200 positioned between a gastric wall 260 (e.g., the stomach) and a portion of a small intestine 270 (e.g., the jejunum). The stent 200 may be a self-expanding stent 200 and may include a radially expanding tubular framework 205 having a radially outward surface 201 and a radially inward surface (not shown in FIG. 4). The radially inward surface may be considered as an example of the radially inward surface 12, as shown in FIG. 2. The term 'radially expanding tubular framework 205' may be referred to as 'tubular framework 205' hereafter. The stent 200 may include a height of 10 millimeters (mm) and an outer diameter (e.g., width) of 20 mm. In some cases, the height of the stent 200 may be 12 mm, 15 mm, 18 mm, or any other suitable height. In some cases, the outer diameter of the stent 200 may be 18 mm, 22 mm, 25 mm, or any other suitable diameter. The tubular framework 205 may include a first end region 210, a second end region 220, and a medial region 230 positioned between the first end region 210 and the second end region 220. The tubular framework 205 may further include a lumen 240 extending from the first end region 210 to the second end region 220. The lumen 240 may be considered as an example of the lumen 14, as shown in FIG. 2. In some cases, the first end region 210 may be a distal end region, and the second end region 220 may be a proximal end region. In some cases, the first end region 210 may be a proximal end region, and the second end region 220 may be a distal end region. The first end region 210 may include a first end 211 and the second end region 220 may include a second end 221. The first end region 210 may extend from the first end 211 to the medial region 230, and the second end region 220 may extend from the second end 221 to the medial region 230. The medial region 230 may define a midpoint in the tubular framework 205, such that the first end region 210 and the second end region 220 may have the same lengths. Alternatively, the medial region 230 may be disposed at a location other than a midpoint, such that the first and second end regions 210, 220 have different lengths.

In some cases, the first end region 210 may include a first flange structure 215 having a first outer diameter and the second end region 220 may include a second flange structure 225 having a second outer diameter. The medial region 230 may be positioned between the first flange structure 215 and the second flange structure 225. The medial region 230 may be configured to engage with a tissue surface, thereby exerting a radial force to aid in prevention of migration of the stent 200. The first end region 210 may further include a third flange structure 235 having a third outer diameter that is longitudinally spaced from the first flange structure 215 a first distance, as indicated by D1. The third flange structure 235 may provide additional radial force to the first end region 210 of the stent 200, thereby preventing migration of the stent 200 from the stomach 260 to the jejunum 270 during peristalsis or turbulence caused by the digestion of a food bolus. The third flange structure 235 may be longitudinally spaced D1 from the first flange structure 215 within a range of 5 mm (millimeters) to 75 mm. In some cases, the third flange structure 235 may be longitudinally spaced D1 from the first flange structure 215 by at least 20 mm. The longitudinal spacing between the first flange structure 215 and the third flange structure 235 may vary for the desired pullout force.

The first flange structure 215, the second flange structure 225, and the third flange structure 235 may be retention members configured to aid in holding the stent 200 in place. Thus, the first, second, and third flange structures 215, 225, 235 may include first, second, and third outer diameters, respectively, sufficient to provide retention strength. For example, the first, second, and third outer diameters of the first, second, and third flange structures 215, 225, 235 may be in the range of 20 mm to 70 mm (millimeters). In some cases, the first, second, and third flange structures 215, 225, 235 may include first, second, and third outer diameters greater than that of the first end 211, the second end 221, and the medial region 230 of the tubular framework 205. In some cases, the first, second, and third outer diameters of the first, second, and third flange structures 215, 225, 235, respectively, may differ from one another. In some cases, third outer diameter of the third flange structure 235 may be greater than the first outer diameter and the second outer diameter of the first flange structure 215 and the second flange structure 225, respectively. In some cases, first flange structure 215 and second flange structure 225 may have approximately the same outer diameter, as indicated in FIG. 4. For example, the third outer diameter of the third flange structure 235 may include an outer diameter of 55 mm and the first outer diameter of the first flange structure 215 and second outer diameter of the second flange structure 225 may include a width of 35 mm. In some cases, the third outer diameter of the third flange structure 235 may include an outer diameter of 45 mm, 60 mm, 65 mm, 70 mm, 45 mm to 70 mm, or any other suitable width. The first outer diameter of the first flange structure 215 and the second outer diameter of the second flange structure 225 may include an outer diameter of 25 mm, 30 mm, 40 mm, 45 mm, 25 mm to 45 mm, or any other suitable width. In some cases, when the third outer diameter of the third flange structure 235 is greater than the first outer diameter of the first flange structure 215, as shown in FIG. 4, risk of migration can be mitigated. For example, if the stent 200 started migrating into the jejunum 270 from the stomach 260, the third flange structure 235 would have a wide enough outer diameter to potentially prevent such migration. In some cases, the first, second, and third outer diameters of the first, second, and third flange structures 215, 225, 235, respectively, may be the same as one another.

In some cases, the first, second, and third flange structures 215, 225, 235 may include any of a variety of shapes, such as concave, convex, disc-shaped, cylindrical (e.g., having a longer longitudinal extent then illustrated), etc., or other configurations, the shape and configuration not being limited by the present disclosure. While it is illustrated that the first flange structure 215 and the third flange structure 235 are positioned near the first end region 210, and the second flange structure 225 is positioned near the second end region 220, it may be contemplated that the first flange structure 215 and the third flange structure 235 are positioned near the second end region 220, and the second flange structure 225 is positioned near the first end region 210. In some cases, it may be contemplated that the tubular framework 205 includes only one flange structure (e.g., the first flange structure 215, the second flange structure 225, or the third flange structure 235).

The tubular framework 205 may include several interconnected struts 206 to form a woven filament braid structure of the tubular framework 205. The struts 206 may be configured to transition from a compressed state to an expanded state. The struts 206 may include a diameter of, for example, 0.0762 mm to 0.3556 mm. The tubular framework 205 may include a coating 207 applied over the struts 206 of the tubular framework 205, thus the entirety of the stent 200 may be covered with the coating 207. The coating 207 may be formed from a silicone and may be configured to prevent leakage of food materials during anastomosis formation. In some cases, the coating 207 may be applied over the struts 206 in the medial region 230. In some cases, the coating 207 may be applied over the struts 206 within the first end region 210 and the medial region 230, and in some cases, the coating 207 may be applied over the struts 206 within the second end region 220 and the medial region 230. These are just examples.

The first flange structure 215 may include a first end 216 and a second end 217, the second flange structure 225 may include a first end 226 and a second end 227, and the third flange structure 235 may include a first end 236 and a second end 237. The first ends 216, 226, 236 and the second ends 217, 227, 237 may be formed by bending the struts 206 of the tubular framework 205 to form atraumatic flange structures (e.g., first flange structure 215, second flange structure 225, third flange structure 235). Thus, the first ends 216, 226, 236 and the second ends 217, 227, 237 may be rounded and atraumatic, such that the first flange structure 215, the second flange structure 225, and the third flange structure 235 are configured to atraumatically engage a bodily tissue (e.g., stomach 20, jejunum 30).

Figure 5:
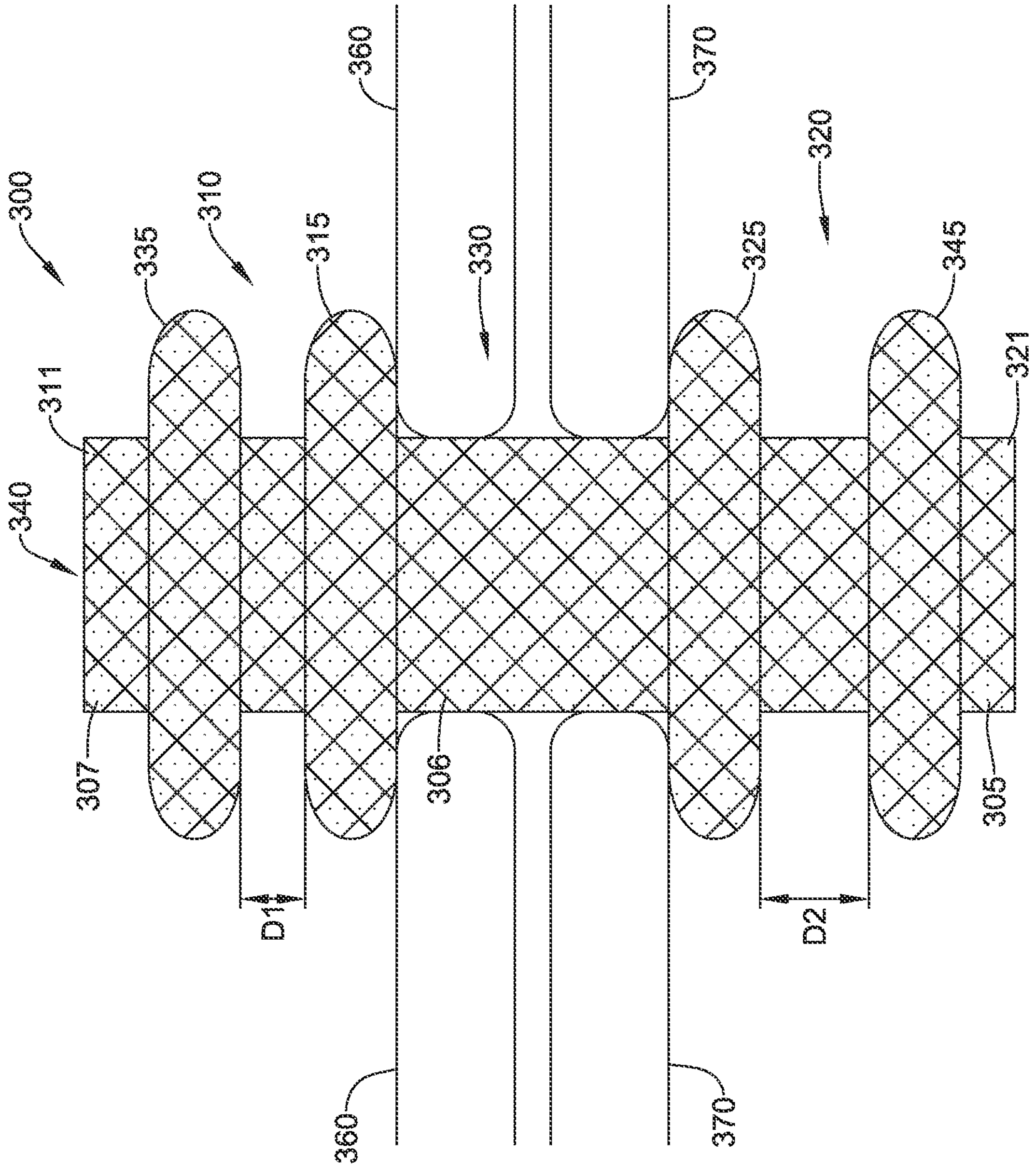
FIG. 5 illustrates an exemplary stent positioned between the gastric wall and the portion of the small intestine.

FIG. 5 illustrates an exemplary stent 300 positioned between a gastric wall 360 (e.g., the stomach) and a portion of a small intestine 370 (e.g., the jejunum). The stent 300 may be a self-expanding stent 300 and may include a radially expanding tubular framework 305 having a radially outward surface 301 and a radially inward surface (not shown in FIG. 5). The radially inward surface may be considered as an example of the radially inward surface 12, as shown in FIG. 2. The term 'radially expanding tubular framework 305' may be referred to as 'tubular framework 305' hereafter. The stent 300 may include a height of 10 mm and an outer diameter (e.g., width) of 20 mm. In some cases, the height of the stent 300 may be 12 mm, 15 mm, 18 mm, 12 mm to 18 mm, or any other suitable height. In some cases, the outer diameter of the stent 300 may be 18 mm, 22 mm, 25 mm, 18 mm to 25 mm, or any other suitable diameter. The tubular framework 305 may include a first end region 310, a second end region 320, and a medial region 330 positioned between the first end region 310 and the second end region 320. The tubular framework 305 may further include a lumen 340 extending from the first end region 310 to the second end region 320. The lumen 340 may be considered as an example of the lumen 14, as shown in FIG. 2. In some cases, the first end region 310 may be a distal end region, and the second end region 320 may be a proximal end region. In some cases, the first end region 310 may be a proximal end region, and the second end region 320 may be a distal end region. The first end region 310 may include a first end 311 and the second end region 320 may include a second end 321. The first end region 310 may extend from the first end 311 to the medial region 330, and the second end region 320 may extend from the second end 321 to the medial region 330. The medial region 330 may define a midpoint in the tubular framework 305, such that the first end region 310 and the second end region 320 may have the same lengths. Alternatively, the medial region 330 may be disposed at a location other than a midpoint, such that the first and second end regions 310, 320 have different lengths.

In some cases, the first end region 310 may include a first flange structure 315 having a first outer diameter and the second end region 320 may include a second flange structure 325 having a second outer diameter. The medial region 330 may be positioned between the first flange structure 315 and the second flange structure 325. The medial region 330 may be configured to engage with a tissue surface, thereby exerting a radial force to aid in prevention of migration of the stent 300. The first end region 310 may further include a third flange structure 335 having a third outer diameter that is longitudinally spaced from the first flange structure 315 a first distance, as indicated by D1. The second end region 320 may further include a fourth flange structure 345 that is longitudinally spaced from the second flange structure 325 a second distance, as indicated by D2. The third flange structure 335 and the fourth flange structure 345 may provide additional radial force to the first end region 310 and the second end region 320, respectively, thereby preventing migration of the stent 300 from the stomach 360 to the jejunum 370 during peristalsis or turbulence caused by the digestion of a food bolus. The third flange structure 335 may be longitudinally spaced D1 from the first flange structure 315 within a range of 5 mm to 75 mm. In some cases, the third flange structure 335 may be longitudinally spaced D1 from the first flange structure 315 by at least 20 mm. The fourth flange structure 345 may be longitudinally spaced D2 from the second flange structure 325 within a range of 5 mm to 75 mm. In some cases, the fourth flange structure 345 may be longitudinally spaced D2 from the second flange structure 325 by at least 20 mm. The longitudinal spacing between the first flange structure 315 and the third flange structure 335, and the longitudinal spacing between the second flange structure 325 and the fourth flange structure 345 may vary for the desired pullout force The first flange structure 315, the second flange structure 325, the third flange structure 335, and the fourth flange structure 345 may be retention members configured to aid in holding the stent 300 in place. Thus, the first, second, third, and fourth flange structures 315, 325, 335, 345 may include first, second, third, and fourth outer diameters, respectively, sufficient to provide retention strength. For example, the first, second, third, and fourth outer diameters of the first, second, third, and fourth flange structures 315, 325, 335, 345 may be in the range of 20 mm to 70 mm. In some cases, the first, second, third, and fourth flange structures 315, 325, 335, 345 may include first, second, third, and fourth outer diameters greater than that of the first end 311, the second end 321, and the medial region 330 of the tubular framework 305. In some cases, the first, second, third, and fourth outer diameters of the first, second, third, and fourth flange structures 315, 325, 335, 345, respectively, may be the same as one another, as indicated in FIG. 4. In some cases, the first, second, third, and fourth outer diameters of the first, second, third, and fourth flange structures 315, 325, 335, 345, respectively, may differ from one another. In some cases, the third outer diameter of the third flange structure 335 may be greater than the first outer diameter, the second outer diameter, and the fourth outer diameter of the first flange structure 315, the second flange structure 325, and the fourth flange structure 345 respectively. For example, the third outer diameter of the third flange structure 335 may include an outer diameter of 55 mm and the first outer diameter of the first flange structure 315, the second outer diameter of the second flange structure 325, and the fourth outer diameter of the fourth flange structure 345 may include a width of 35 mm. In some cases, the third outer diameter of the third flange structure 335 may include an outer diameter of 45 mm, 60 mm, 65 mm, 70 mm, 45 mm to 70 mm, or any other suitable width. The first outer diameter of the first flange structure 315, the second outer diameter of the second flange structure 325, and the fourth outer diameter of the fourth flange structure 345 may include an outer diameter of 25 mm, 30 mm, 40 mm, 45 mm, or any other suitable width.

In some cases, the first, second, third, and fourth flange structures 315, 325, 335, 345 may include any of a variety of shapes, such as concave, convex, disc-shaped, cylindrical (e.g., having a longer longitudinal extent then illustrated), etc., or other configurations, the shape and configuration not being limited by the present disclosure. While it is illustrated that the first flange structure 315 and the third flange structure 335 are positioned near the first end region 310, and the second flange structure 325 and the fourth flange structure 345 are positioned near the second end region 320, it may be contemplated that the first flange structure 315 and the third flange structure 335 are positioned near the second end region 320, and the second flange structure 325 and the fourth flange structure 345 are positioned near the first end region 310. In some cases, it may be contemplated that the tubular framework 305 includes only one flange structure (e.g., the first flange structure 315, the second flange structure 325, the third flange structure 335, or the fourth flange structure 345).

The tubular framework 305 may include several interconnected struts 306 to form a woven filament braid structure of the tubular framework 305. The struts 306 may be configured to transition from a compressed state to an expanded state. The struts 306 may include a diameter of, for example, 0.0762 mm to 0.3556 mm. The tubular framework 305 may include a coating 307 applied over the struts 306 of the tubular framework 305, thus the entirety of the stent 200 may be covered with the coating 307. The coating 307 may be formed from a silicone and may be configured to prevent leakage of food materials during anastomosis formation. In some cases, the coating 307 may be applied over the struts 306 in the medial region 330. In some cases, the coating 307 may be applied over the struts 306 within the first end region 310 and the medial region 330, and in some cases, the coating 307 may be applied over the struts 306 within the second end region 320 and the medial region 330. These are just examples.

Figure 6:
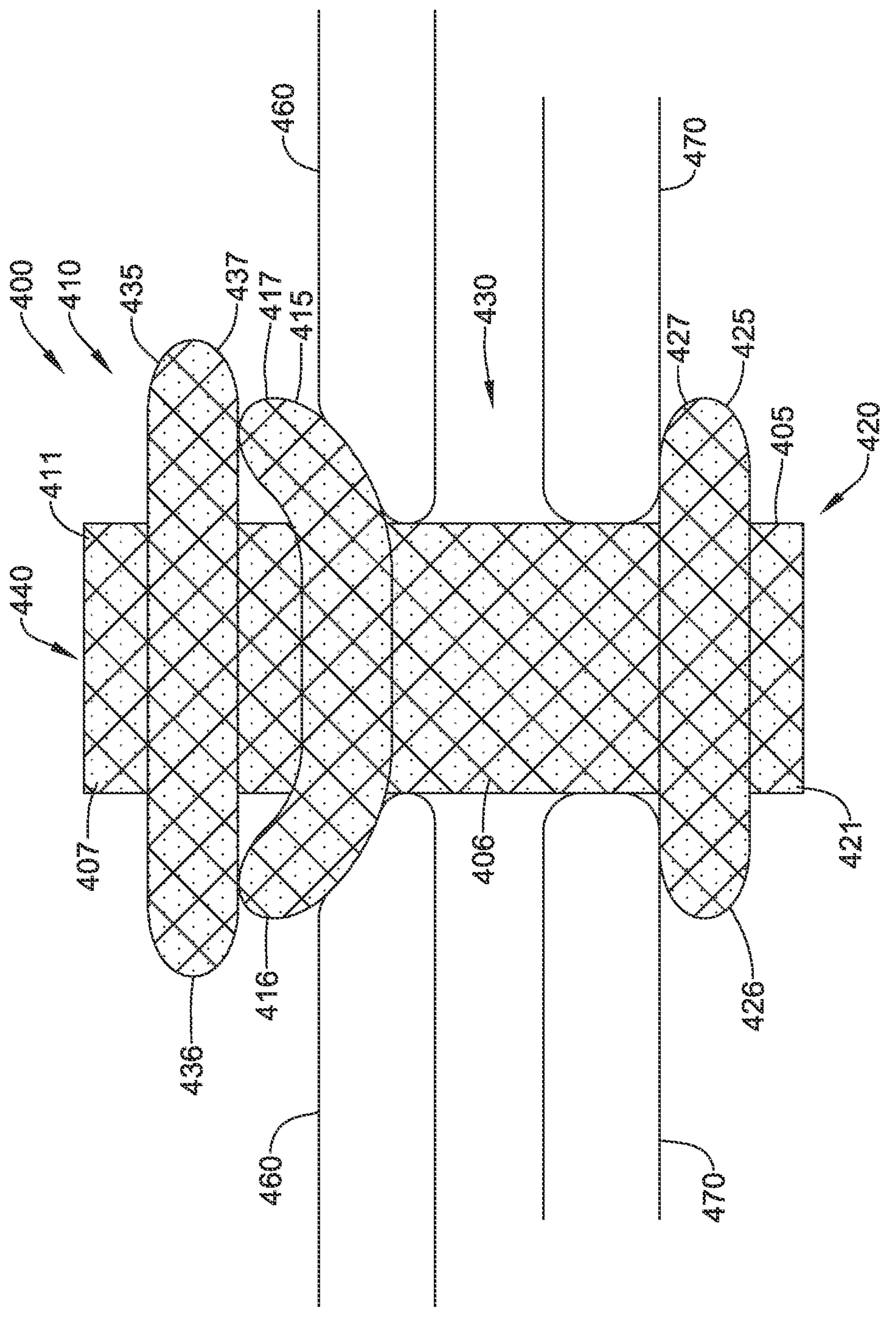
FIG. 6 illustrates an exemplary stent positioned between the gastric wall and the portion of the small intestine.

FIG. 6 illustrates an exemplary stent 400 positioned between a gastric wall 460 (e.g., the stomach) and a portion of a small intestine 470 (e.g., the jejunum). The stent 400 may be a self-expanding stent 400 and may include a radially expanding tubular framework 405 having a radially outward surface 401 and a radially inward surface (not shown in FIG. 6). The radially inward surface may be considered as an example of the radially inward surface 12, as shown in FIG. 2. The term 'radially expanding tubular framework 405' may be referred to as 'tubular framework 405' hereafter. The stent 400 may include a height of 10 mm and an outer diameter (e.g., width) of 20 mm. In some cases, the height of the stent 400 may be 12 mm, 15 mm, 18 mm, 12 mm to 18 mm, or any other suitable height. In some cases, the outer diameter of the stent 400 may be 18 mm, 22 mm, 25 mm, 18 mm to 25 mm, or any other suitable diameter. The tubular framework 405 may include a first end region 410, a second end region 420, and a medial region 430 positioned between the first end region 410 and the second end region 420. The tubular framework 405 may further include a lumen 440 extending from the first end region 410 to the second end region 420. The lumen 440 may be considered as an example of the lumen 14, as shown in FIG. 2. In some cases, the first end region 410 may be a distal end region, and the second end region 420 may be a proximal end region. In some cases, the first end region 410 may be a proximal end region, and the second end region 420 may be a distal end region. The first end region 410 may include a first end 411 and the second end region 420 may include a second end 421. The first end region 410 may extend from the first end 411 to the medial region 430, and the second end region 420 may extend from the second end 421 to the medial region 430. In some cases, the medial region 430 may define a midpoint in the tubular framework 405, such that the first end region 410 and the second end region 420 may have the same lengths. In some cases, as indicated in FIG. 6, the medial region 430 may be disposed at a location other than a midpoint, such that the first and second end regions 410, 420 have different lengths.

In some cases, the first end region 410 may include a first flange structure 415 having a first outer diameter and the second end region 420 may include a second flange structure 425 having a second outer diameter. The medial region 430 may be positioned between the first flange structure 415 and the second flange structure 425. The medial region 430 may be configured to engage with a tissue surface, thereby exerting a radial force to aid in prevention of migration of the stent 400. The first end region 410 may further include a third flange structure 435 having a third outer diameter that is longitudinally spaced from the first flange structure 415 a first distance, as indicated by D1. The third flange structure 435 may provide additional radial force to the first end region 410 of the stent 400, thereby preventing migration of the stent 400 from the stomach 460 to the jejunum 470 during peristalsis or turbulence caused by the digestion of a food bolus. The third flange structure 435 may be longitudinally spaced D1 from the first flange structure 415 within a range of 5 mm to 75 mm. In some cases, the third flange structure 435 may be longitudinally spaced D1 from the first flange structure 415 by at least 20 mm. The longitudinal spacing between the first flange structure 415 and the third flange structure 435 may vary for the desired pullout force.

The first flange structure 415, the second flange structure 425, and the third flange structure 435 may be retention members configured to aid in holding the stent 400 in place. Thus, the first, second, and third flange structures 415, 425, 435 may include first, second, and third outer diameters, respectively, sufficient to provide retention strength. For example, the first, second, and third outer diameters of the first, second, and third flange structures 415, 425, 435 may be in the range of 20 mm to 70 mm. In some cases, the first, second, and third flange structures 415, 425, 435 may include first, second, and third outer diameters greater than that of the first end 411, the second end 421, and the medial region 430 of the tubular framework 05. In some cases, the first, second, and third outer diameters of the first, second, and third flange structures 415, 425, 435, respectively, may be the same as one another. In some cases, the first, second, and third outer diameters of the first, second, and third flange structures 415, 425, 435, respectively, may differ from one another, as indicated in FIG. 6. In some cases, third outer diameter of the third flange structure 435 may be greater than the first outer diameter and the second outer diameter of the first flange structure 415 and the second flange structure 425, respectively. For example, the third outer diameter of the third flange structure 435 may include an outer diameter of 55 mm and the first outer diameter of the first flange structure 415 and second outer diameter of the second flange structure 425 may include a width of 35 mm. In some cases, the third outer diameter of the third flange structure 435 may include an outer diameter of 45 mm, 60 mm, 65 mm, 70 mm, 45 mm to 70 mm, or any other suitable width. The first outer diameter of the first flange structure 415 and the second outer diameter of the second flange structure 425 may include an outer diameter of 25 mm, 30 mm, 40 mm, 45 mm, 25 mm to 45 mm, or any other suitable width. In some cases, when the third outer diameter of the third flange structure 435 is greater than the first outer diameter of the first flange structure 415, as shown in FIG. 6, the risk of migration can be mitigated. For example, if the stent 400 started migrating into the jejunum 470 from the stomach 460, the third flange structure 435 would have a wide enough outer diameter to prevent such migration.

In some cases, the first, second, and third flange structures 415, 425, 435 may include any of a variety of shapes, such as concave, convex, disc-shaped, cylindrical (e.g., having a longer longitudinal extent then illustrated), etc., or other configurations, the shape and configuration not being limited by the present disclosure. While it is illustrated that the first flange structure 415 and the third flange structure 435 are positioned near the first end region 410, and the second flange structure 425 is positioned near the second end region 420, it may be contemplated that the first flange structure 415 and the third flange structure 435 are positioned near the second end region 420, and the second flange structure 425 is positioned near the first end region 10. In some cases, it may be contemplated that the tubular framework 405 includes only one flange structure (e.g., the first flange structure 415, the second flange structure 425, or the third flange structure 435).

The tubular framework 405 may include several interconnected struts 406 to form a woven filament braid structure of the tubular framework 405. The struts 406 may be configured to transition from a compressed state to an expanded state. The struts 406 may include a diameter of, for example, 0.0762 mm to 0.3556 mm. The tubular framework 405 may include a coating 407 applied over the struts 406 of the tubular framework 405, thus the entirety of the stent 400 may be covered with the coating 407. The coating 407 may be formed from a silicone and may be configured to prevent leakage of food materials during anastomosis formation. In some cases, the coating 407 may be applied over the struts 406 in the medial region 430. In some cases, the coating 407 may be applied over the struts 406 within the first end region 410 and the medial region 430, and in some cases, the coating 407 may be applied over the struts 406 within the second end region 420 and the medial region 430. These are just examples.

The first flange structure 415 may include a first end 416 and a second end 417, the second flange structure 425 may include a first end 426 and a second end 427, and the third flange structure 435 may include a first end 436 and a second end 437. The first ends 416, 426, 436 and the second ends 417, 427, 437 may be formed by bending the struts 406 of the tubular framework 405 to form atraumatic flange structures (e.g., first flange structure 415, second flange structure 425, third flange structure 435). Thus, the first ends 416, 426, 436 and the second ends 417, 427, 437 may be rounded and atraumatic, such that the first flange structure 415, the second flange structure 425, and the third flange structure 435 are configured to atraumatically engage a bodily tissue (e.g., stomach 20, jejunum 30).

In the example shown in FIG. 6, the first end 416 of the first flange structure 415 and the second end 417 of the first flange structure 415 may curve toward the third flange structure 435 (and away from the second flange structure 425) such that the first end 416 and the second end 417 of the first flange structure 415 may be configured to engage with a surface of the third flange structure 435. As the first end 416 and the second end 417 engage with the third flange structure 435, the third flange structure 435 provides resistance during peristalsis, thereby preventing migration of the stent 400 from the stomach 460 into the jejunum 470.

The stent 10, 100, 200, 300, 400 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of stent 10, 100, 200, 300, 400 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10, 100, 200, 300, 400 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent 10, 100, 200, 300, 400 to achieve the same result.

In some embodiments, a degree of Magnetic Resonance Imaging (MRI) compatibility is imparted into stent 10, 100, 200, 300, 400. For example, stent 10, 100, 200, 300, 400, or portions thereof, may be made of a material that does not substantially distort the image and create substantial artifacts (i.e., gaps in the image). Certain ferromagnetic materials, for example, may not be suitable because they may create artifacts in an MRI image. The stent 10, 100, 200, 300, 400, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, platinol, and the like, and others.

It is to be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent comprising:

a radially expanding tubular framework having a radially outward surface, a radially inward surface, a first end region, a second end region, a medial region positioned between the first end region and the second end region, and a lumen extending from the first end region to the second end region;

a first flange structure positioned near the first end region; and a second flange structure positioned near the second end region;

wherein the first end region includes a third flange structure, wherein the third flange structure is positioned near the first end region, and wherein the first flange structure is configured to curve toward the third flange structure such that a first end and a second end of the first flange structure are configured to engage with the third flange structure.

2. The stent of claim 1, wherein the stent is a self-expanding stent.

3. The stent of claim 1, wherein the first flange and the second flange are configured to atraumatically engage a bodily tissue.

4. The stent of claim 1, wherein the first flange structure includes a first outer diameter, the second flange structure includes a second outer diameter, and the third flange structure includes a third outer diameter, wherein the first outer diameter, the second outer diameter, and the third outer diameter differ from one another.

5. The stent of claim 4, wherein the third outer diameter is greater than the first outer diameter and the second outer diameter.

6. The stent of claim 1, wherein the first, second, and third flange structures each have an outer diameter greater than an outer diameter of the medial region.

7. The stent of claim 1, wherein the radially expanding tubular framework is formed from a woven filament braid.

8. The stent of claim 7, wherein a braid angle of the third flange structure differs from a braid angle of the first and second flange structures.

9. The stent of claim 1, wherein the second end region includes a fourth flange structure.

10. The stent of claim 1, wherein the third flange structure is longitudinally spaced from the first flange structure within a range of 5 mm to 75 mm.

11. The stent of claim 1, wherein the third flange structure is longitudinally spaced from the first flange structure by at least 20 mm.

12. A stent comprising:

a radially expanding tubular framework formed from a woven filament braid having a first end region, a second end region, a medial region positioned between the first end region and the second end region, and a lumen extending from the first end region to the second end region;

a first flange structure having a first outer diameter positioned near the first end region;

a second flange structure having a second outer diameter positioned near the second end region; and a third flange structure having a third outer diameter positioned near the first end region;

wherein the third flange structure is longitudinally spaced from the first flange structure; and wherein the first flange structure is configured to curve toward the third flange structure such that a first end and a second end of the first flange structure are configured to engage with the third flange structure; and wherein the third outer diameter is greater than the first outer diameter and the second outer diameter.

13. The stent of claim 12, wherein the first outer diameter, the second outer diameter, and the third outer diameter are each greater than an outer diameter of the medial region.

14. The stent of claim 12, wherein a braid angle of the third flange structure differs from a braid angle of the first and second flange structures.

15. The stent of claim 12, wherein the third flange structure is longitudinally spaced from the first flange structure within a range of 5 mm to 75 mm.

16. The stent of claim 12, wherein the third flange structure is longitudinally spaced from the first flange structure by at least 20 mm.

17. A stent comprising:

a radially expanding tubular framework formed from a woven filament braid having a first end region, a second end region, a medial region positioned between the first end region and the second end region, and a lumen extending from the first end region to the second end region;

a first flange structure having a first outer diameter positioned near the first end region;

a second flange structure having a second outer diameter positioned near the second end region; and a third flange structure having a third outer diameter positioned near the first end region;

wherein the third flange structure is longitudinally spaced from the first flange structure within a range of 5 mm to 75 mm; and wherein the first flange structure is configured to curve toward the third flange structure such that a first end and a second end of the first flange structure are configured to engage with the third flange structure.

18. The stent of claim 17, wherein the third outer diameter is greater than the first outer diameter and the second outer diameter.

* * * * *